United States Patent [19]

Schulz et al.

[11] Patent Number: 5,008,446
[45] Date of Patent: Apr. 16, 1991

[54] PREPARATION OF PHENOXY-SUBSTITUTED ESTERS AND INTERMEDIATES THEREFOR

[75] Inventors: Guenter Schulz, Ludwigshafen; Hubert Sauter, Mannheim, both of Fed. Rep. of Germany

[73] Assignee: BASF Aktiengesellschaft, Ludwigshafen, Fed. Rep. of Germany

[21] Appl. No.: 365,559

[22] Filed: Jun. 13, 1989

Related U.S. Application Data

[62] Division of Ser. No. 129,710, Dec. 7, 1987, Pat. No. 4,870,205.

[30] Foreign Application Priority Data

Dec. 13, 1986 [DE] Fed. Rep. of Germany ....... 3642632

[51] Int. Cl.$^5$ .............................................. C07C 67/02
[52] U.S. Cl. ..................................... 560/254; 560/255
[58] Field of Search ................................ 560/255, 254

[56] References Cited

U.S. PATENT DOCUMENTS 4,380,546  4/1983  Sauter et al. ......................... 424/269

FOREIGN PATENT DOCUMENTS 0040350  9/1983  European Pat. Off. .
3606947  4/1987  Fed. Rep. of Germany .

OTHER PUBLICATIONS

Mar., *Advanced Organic Chemistry*, 2nd Edition, pp. 439–440 (1977).

Primary Examiner—Bruce Gray
Attorney, Agent, or Firm—John H. Shurtleff

[57] ABSTRACT

Compounds of the formula I

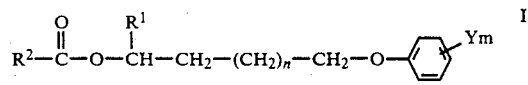

where $R^1$ is

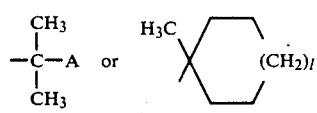

where A is $C_1$–$C_4$-alkyl, phenyl or $C_7$–$C_{12}$-aralkyl and l is 0 or 1, $R^2$ is $C_1$–$C_4$-alkyl, n is 0, 1, 2 or 3, m is 1, 2 or 3 and Y is hydrogen, fluorine, chlorine, bromine, $C_1$–$C_3$-alkyl, $C_1$–$C_3$-alkoxy, trifluoromethyl, phenyl or phenoxy, and, when m is greater than 1, the individual atoms or groups Y are identical or different, are prepared by a process in which, in a first stage, a diester of the formula II

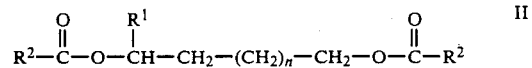

is hydrolyzed with one equivalent of an aqueous alkali metal hydroxide to give the alcohol of the formula IIIa

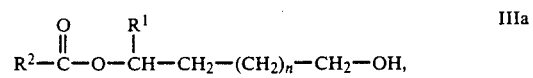

in a second stage this alcohol is converted with a halogenating agent or a sulfonyl chloride or bromide into a compound of the formula IIIb

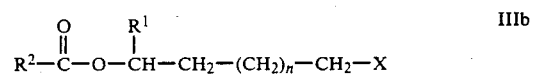

where X is a nucleophilically displaceable leaving group, such as chlorine, bromine, mesyl or tosyl, and then, in a third stage, the compound IIIb is reacted with a phenolate of the formula IV

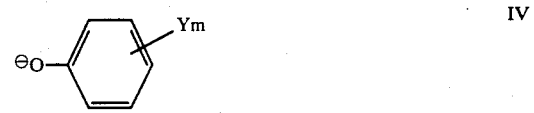

where y and m have the abovementioned meanings, in the presence of an aprotic solvent to give compound I. Furthermore, diesters of the formula II and a process for their preparation are provided, the said diesters being prepared by reacting a lactone of the formula V

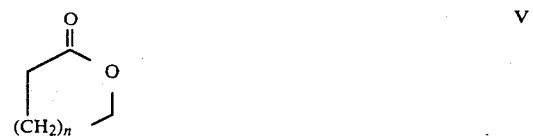

with a Grignard compound VI

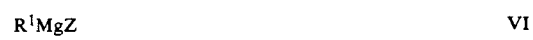

where Z is chlorine or bromine, in a nonpolar organic solvent, from 2 to 3 moles of the Grignard compound being used per mole of lactone, and the reaction mixture then being treated with from 2 to 3 moles of anhydride VII

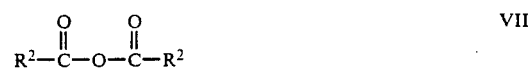

per mole of lactone.

6 Claims, No Drawings

PREPARATION OF PHENOXY-SUBSTITUTED ESTERS AND INTERMEDIATES THEREFOR

This application is a division, of application Ser. No. 129,710, filed Dec. 7, 1987 now U.S. Pat. No. 4,870,205.

The present invention relates to a process for the preparation of phenoxy-substituted esters I

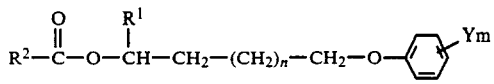

where $R^1$ is

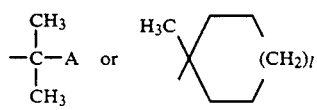

where A is $C_1$-$C_4$-alkyl, phenyl or $C_7$-$C_{12}$-aralkyl and l is 0 or 1, $R^2$ is $C_1$-$C_4$-alkyl, n is 0, 1, 2 or 3, m is 1, 2 or 3 and Y is hydrogen, fluorine, chlorine, bromine, $C_1$-$C_3$-alkyl, $C_1$-$C_3$-alkoxy, trifluoromethyl, phenyl or phenoxy, and, when m is greater than 1, the individual atoms or groups Y are identical or different, intermediates for this purpose and processes for the preparation of the intermediates.

The compounds I are useful starting materials for the production of crop protection agents, in particular phenoxytriazolylalkanol compounds, eg. 8-(2-fluorophenoxy)-4-(1,2,4-triazol-1-yl)-3-hydroxy-2,2-dimethyloctane, as described in the previous Application P 36 06 947.7 (O.Z. 0050/38303) and in European Patent No. 40 350. They have been synthesized to date by reacting aldehydes, eg. pivalaldehyde, with Grignard compounds, eg. 4-(2-fluorophenoxy)-butylmagnesium chloride, and reacting the resulting alcohols with appropriate anhydrides. This procedure has the disadvantages that, on the one hand, a large proportion of the Grignard compound is lost as a result of hydride transfer to the sterically hindered aldehyde with formation of the terminal alkene and, on the other hand, the halide from which the Grignard compound is derived is not readily obtainable.

It is an object of the present invention to provide a simple and economical synthetic route for the compounds I.

We have found that this object is achieved and that the compounds I defined at the outset can advantageously be prepared by a process in which, in a first stage, a diester of the formula II

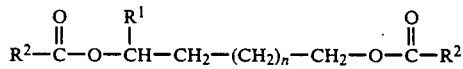

is hydrolyzed with one equivalent of an aqueous alkali metal hydroxide to give the alcohol of the formula IIIa

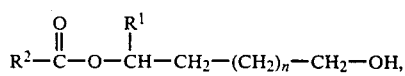

in a second stage this alcohol is converted with a halogenating agent or a sulfonyl chloride or bromide into a compound of the formula IIIb

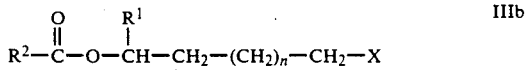

where X is a nucleophilically displaceable leaving group, such as chlorine, bromine, mesyl or tosyl, and then, in a thrid stage, the compound IIIb is reacted with a phenolate of the formula IV

where Y and m have the abovementioned meanings, in the presence of an aprotic solvent to give compound I.

In the compounds I, II and III, $R^1$ is 1-methylcyclohexyl or —cyclopentyl or the group —$C(CH_3)_2$—A, where A is $C_1$-$C_4$-alkyl, eg. methyl, ethyl, n-propyl, isopropyl or n-butyl, phenyl or $C_7$-$C_{12}$-aralkyl, eg. benzyl or phenylethyl. $R^2$ is a branched or, preferably, straight-chain $C_1$-$C_4$-alkyl group, eg. methyl, ethyl, n-propyl or n-butyl. The indices n and m in compound I are each the integer 1, 2 or 3 and n can also be 0. Preferred compounds I and II are those in which $R^1$ is tert-butyl, $R^2$ is methyl or ethyl and n is 3.

Y is hydrogen, fluorine, chlorine, bromine, $C_1$-$C_3$-alkyl or $C_1$-$C_3$-alkoxy, eg. methyl, ethyl, propyl, isopropyl, methoxy, ethoxy, propoxy or isopropoxy.

In the first stage of the process, the diester II is hydrolyzed by means of one equivalent of an aqueous alkali metal hydroxide, eg. sodium hydroxide or potassium hydroxide, or another base, such as an alkaline earth metal hydroxide or a carbonate, to give the alcohol IIIa. The hydrolysis can be carried out with or without a solubilizer. Examples of suitable solubilizers are short-chain aliphatic alcohols, such as methanol, ethanol, propanol, isopropanol or butanol. The reaction temperature is not particularly critical and is in general from 20° to 100° C. Since the reaction takes place more rapidly at elevated temperatures than at room temperature, temperatures of about 50°-80° C. are preferred.

The alcohols thus obtained are then isolated from the reaction mixture in a conventional manner, for example by extraction, and are converted, after prior purification or preferably directly, with a halogenating agent or sulfonyl chloride or bromide into the compound IIIb, where X is a nucleophilically displaceable leaving group, eg. mesyl or tosyl or preferably chlorine or bromine.

Halogenating agents for replacing the hydroxyl group are, in particular, inorganic acid halides, such as phosphorus pentachloride and, preferably, phosphorus trichloride, phosphorus tribromide, thionyl chloride and thionyl bromide. This reaction can be carried out in the presence or absence of a diluent, for example an inert organic solvent, such as benzene, toluene or xylene, at from 50° to 100° C. Typical reaction conditions are described in, for example, Houben-Weyl, Methoden der organischen Chemie, Volume V/3, 1962, pages 862-864, and Volume V/4, 1960, page 389 et seq.

The conversion of the hydroxyl group to a sulfonic ester by means of a sulfonyl chloride or sulfonyl bromide, such as a para-toluenesulfonyl halide or methanesulfonyl halide, can be effected in a conventional manner, for example as described in Houben-Weyl, Methoden der organischen Chemie, Volume V/4, 1960, page 408 et seq., in the presence or absence of aprotic diluents, such as toluene or xylene, and with or without an acid acceptor, eg. pyridine, quinoline or an alkali metal carbonate.

In a third stage of the process, the compound IIIb is reacted, preferably after purification by distillation, with a phenolate IV in the presence of an aprotic solvent, such as tetramethylurea, N,N-dimethylethylene or —propyleneurea, dimethyl sulfoxide or, in particular, dimethylformamide, N-methylpyrrolidone or xylene. The phenolate can be prepared in situ from the corresponding phenol by means of a suitable base capable of deprotonating the phenols, for example an alkali metal hydroxide, such as sodium hydroxide or potassium hydroxide. It is of course also possible to prepare the phenolate separately from the phenol and a base, such as an alkali metal hydroxide, or a $C_1$-$C_4$-alcoholate, such as a methylate or ethylate, and then to react the said phenolate with the compound IIIb. The phenolates contain from 1 to 3 identical or different substituents Y, which are as defined above. $C_1$-$C_3$-alkyl or alkoxy radicals are, for example, methyl, ethyl, propyl, isopropyl, methoxy, ethoxy, propoxy or isopropoxy.

A particularly advantageous embodiment of the process is illustrated using the diacetate

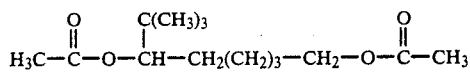

as an example. This compound can be hydrolyzed to the monoacetate

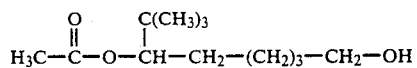

by stirring with one equivalent of 50% strength sodium hydroxide solution at from 60° to 80° C. and, after isolation from the reaction mixture, the monoacetate can be converted to the chloride

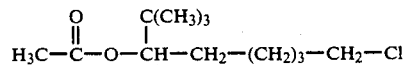

with from 1 to 2 moles of thionyl chloride per mole of monoacetate at from 60° to 80° C. in xylene as a solvent. After any excess thionyl chloride has been separated off from the reaction mixture, or advantageously after purification of this intermediate by distillation, it is possible to carry out the reaction with a stoichiometric amount or an excess of a phenolate of the general formula IV in xylene or, preferably, dimethylformamide as a solvent at from 60° to 120° C. to give the desired phenoxy compound, the said phenolate being obtained, for example, by deprotonation of the corresponding phenol with an alkali metal hydroxide.

The diester of the formula II

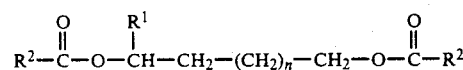

where $R^1$, $R^2$ and n have the meanings stated in claim 1, which is required for the reaction sequence described, is obtained by reacting a lactone of the formula V

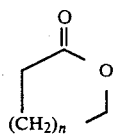

with a Grignard compound VI

where Z is chlorine or bromine, in a nonpolar organic solvent, from 2 to 3 moles of the Grignard compound being used per mole of lactone, and then treating the reaction mixture with from 2 to 3 moles of an anhydride VII

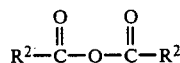

per mole of lactone.

It is surprising that this process takes place smoothly, since it is known that, although Grignard compounds can be reacted with aldehydes and ketones to give carbinols in good yields, the reaction with acid derivatives, such as acid chlorides, anhydrides and esters, generally does not lead to pure products (cf. Jerry March, Advanced Organic Chemistry, 2nd Ed., McGraw-Hill 1977, pages 439 and 440, and the literature cited therein). As a rule, product mixtures formed, for example, by double Grignard addition reactions are obtained. Furthermore, partially formed products may undergo a secondary reaction with unconverted starting materials. In order to ensure a smooth reaction with acid derivatives, it is necessary either to add a catalyst or to replace the Grignard compounds with other organometallic compounds.

In the Grignard compounds used for the novel process, $R^1$ is the radical $R^1$ defined in claim 1, preferably a tertiary alkyl group, in particular tertbutyl. For reasons of cost, alkylmagnesium chlorides are preferred.

Lactones V are, for example, $\gamma$-, $\delta$- or $\epsilon$-lactones, such as $\gamma$-butyrolactone, $\delta$-valerolactone and $\delta$-caprolactone.

The Grignard compound can advantageously be prepared in an inert solvent, such as an ether, eg. diethyl ether or tetrahydrofuran, from the chloride $R^1Cl$ or bromide $R^1Br$ and magnesium in a conventional manner. The Grignard compound dissolved in the ether, preferably in from 1 to 5 moles per mole of Grignard compound, is reacted with the lactone directly or after removal of any excess ether, possible solvents and diluents for this reaction being nonpolar organic compounds, such as alkanes of 4 to 8 carbon atoms, or, advantageously, aromatics, such as benzene, toluene or, in particular, xylene. The amount of solvent or diluent should advantageously be such that the reaction mixture is readily stirrable and the heat evolved in the exothermic reaction can be readily removed. By means of preliminary experiments, the optimum amount of solvent for each reaction can easily be determined. Where xylene is used as the solvent, amounts of about 1 liter per mole of Grignard compound have proven satisfactory.

From 2 to 3 moles of the Grignard compound are reacted per mole of lactone. The reaction temperature may in general be about 20°-100° C., in particular 40°-90° C.

The reaction mixture is then reacted with an anhydride IV, for example the anhydride of acetic acid, propionic acid, butyric acid or valeric acid, at from 20° to 100° C., in particular from 30° to 60° C., from 2 to 3 moles of anhydride being added per mole of lactone.

After the reaction mixture has been worked up in a conventional manner, for example by the addition of water, phase separation and removal of the solvent, the desired diester II is generally obtained in sufficient purity, so that it can be used directly for the subsequent hydrolysis. Purification by distillation may of course be carried out beforehand.

Regarding the further processing of the intermediates II to give crop protection agents, as described in, for example, earlier Application P 36 06 947.7, the novel process is of particular interest for the preparation of compounds in which $R^1$ is tert-butyl, $R^2$ is methyl or ethyl and n is 3.

The individual process steps are illustrated below by way of example for the preparation of the acetate of 8-(2-fluorophenoxy)-2,2-dimethylocatan-3-ol.

EXAMPLE (1) Reaction of caprolactone with tert-butylmagnesium chloride and acetic anhydride to give the diacetate

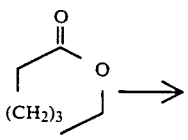

A

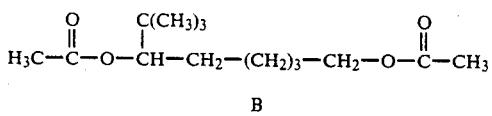

B 1.31 moles of caprolactone A in 100 ml of xylene are introduced with vigorous stirring in the course of about 2 minutes at an initial temperature of 40° C. into 2.89 moles of the tert-butyl Grignard compound with 2.89 moles of tetrahydrofuran in xylene, giving a total volume of 3 l. With removal of heat by cooling with ice-/water and refluxing of the solvent, the highly exothermic reaction results in a final temperature of 80°-90° C. Stirring is continued for 1 hour and 2.89 moles of acetic anhydride are added at about 30° C. at a rate such that the temperature does not substantially exceed about 60° C. After about 1 hour, 1.5 l of water are added and the phases are separated. The organic phase is evaporated down, resulting in a crude yield of 319.3 g, which corresponds to a purity of about 64% and a yield of diacetate B of 60% according to gas chromatographic analysis. A corresponding amount can be isolated by distillation (bp$_{18}$: 163° C.). However, the crude product can also be used directly for the hydrolysis.

$^1$H-NMR (CDCl$_3$) 1.9 s (9H), 1.2-1.75 m (8H), 2.02 s (3H), 2.05 s (3H), 4.05 t (2H), 4.72 dd (1H).

(2) Hydrolysis of the diacetate B and halogenation of the monoacetate

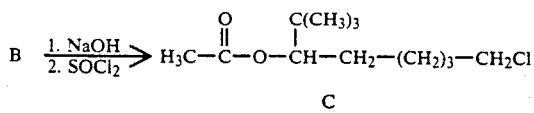

(a) Hydrolysis 0.81 mole of 50% strength sodium hydroxide solution is added dropwise to 0.81 mole of diacetate B at 65°-75° C. in the course of 60 minutes with vigorous stirring. The reaction is terminated at a yield of monoacetate of about 95%, according to gas chromatography. The phases are separated and the aqueous phase is extracted twice with xylene. For drying, the monoacetate phase combined with the xylene extracts is predried with Na$_2$SO$_4$ and then subjected to incipient distillation.

(b) Chlorinahion:

Solvent is added in an amount such that about a 30% strength solution of monoacetate in xylene is formed. About 1.5 equivalents of thionyl chloride are added dropwise at about 80° C. When the evolution of gas has ended, low boiling components are first removed under reduced pressure. After neutralization with bicarbonate, the mixture is distilled under reduced pressure to give 161 g (0.68 mole) of product C (bp$_2$: 145°-150° C.)

$^1$H-NMR (CDCl$_3$): 1.9 s (9H), 1.25-1.8 m (8H), 2.1 s (3H), 3.62 t (2H), 4.75 m (1H).

(3) Conversion of the chloromonoacetate C to the phenoxy-substituted compound D

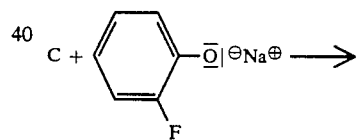

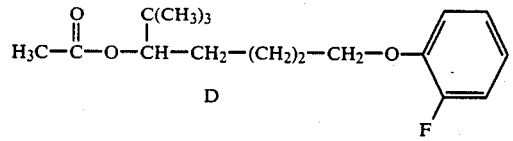

D 0.95 mole of C is added dropwise to 0.95 mole of sodium 2-fluorophenolate in 300 ml of dry dimethylformamide at 70° C. The mixture is stirred at 80° C. and the reaction monitored by thin-layer chromatography. The end point is indicated by consumption of all of the phenolate. The mixture is filtered and dimethylformamide is substantially distilled off under reduced pressure. Residual dimethylformamide is removed by taking up the product in methylene chloride and extracting with water. Removal of the solvent under reduced pressure gives 265 g (0.85 mole) of product D (bp$_{0.1}$: 110° C.).

$^1$H-NMR (CDCl$_3$): 1.9 s (9H), 1.2-1.9 m (8H), 2.08 s (3H), 4.0 t (2H), 4.75 dd (1H), 6.8-7.15 m (4H).

We claim:

1. A process for the preparation of a compound of the formula I

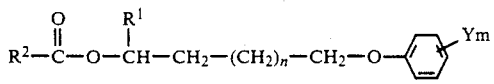

where $R^1$ is

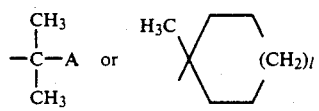

where A is $C_1$-$C_4$-alkyl, phenyl or $C_7$-$C_{12}$-aralkyl and l is 0 or 1, $R^2$ is $C_1$-$C_4$-alkyl, n is 0, 1, 2 or 3, m is 1, 2 or 3 and Y is hydrogen, fluorine, chlorine, bromine, $C_1$-$C_3$-alkyl, $C_1$-$C_3$-alkoxy, trifluoromethyl, phenyl or phenoxy, and, when m is greater than 1, the individual atoms or groups Y are identical or different, wherein, in a first stage, a diester of the formula II

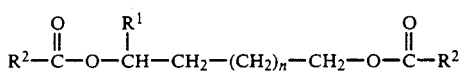

is hydrolyzed with one equivalent of an aqueous alkali metal hydroxide to give the alcohol of the formula IIIa

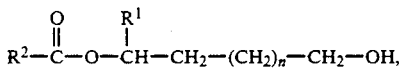

in a second stage this alcohol is converted with a halogenating agent or a sulfonyl chloride or bromide into a compound of the formula IIIb

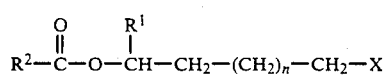

where X is substituted as a nucleophilically displaceable leaving group, and then, in a third stage, the compound IIIb is reacted with a phenolate of the formula IV

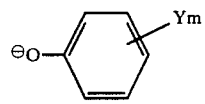

where Y and m have the abovementioned meanings, in the presence of an aprotic solvent to give compound I.

2. A process as claimed in claim 1, wherein $R^1$ is tert-butyl, $R^2$ is methyl or ethyl and n is 3.

3. A process as claimed in claim 1, wherein thionyl chloride or bromide, phosphorus tribromide or phosphorus trichloride, is used as the halogenating agent in the second stage.

4. A process as claimed in claim 1, wherein the phenolate is prepared in situ in the third reaction stage from the corresponding phenol by means of a base.

5. A process as claimed in claim 1, wherein dimethylformamide, N-methylpyrrolidone or xylene is used as the solvent in the third stage.

6. A process as claimed in claim 1, wherein the leaving group X of the compound IIIb is selected from the group consisting of chlorine, bromine, mesyl and tosyl.

* * * * *